US012590940B2

(12) United States Patent
Coskun et al.

(10) Patent No.: US 12,590,940 B2
(45) Date of Patent: Mar. 31, 2026

(54) SYSTEM AND METHOD FOR ESTIMATING RESERVOIR FLUID CONTAMINATION

(71) Applicant: Baker Hughes Oilfield Operations LLC, Houston, TX (US)

(72) Inventors: Sefer Coskun, Houston, TX (US); Anup Hunnur, Houston, TX (US); Alireza Shahkarami, Houston, TX (US); Junjie Yang, Houston, TX (US); Emiliano Hall, Jandakot (AU)

(73) Assignee: Baker Hughes Oilfield Operations LLC, Houston, TX (US)

( * ) Notice: Subject to any disclaimer, the term of this patent is extended or adjusted under 35 U.S.C. 154(b) by 516 days.

(21) Appl. No.: 18/115,367

(22) Filed: Feb. 28, 2023

(65) Prior Publication Data

US 2023/0288396 A1 Sep. 14, 2023

Related U.S. Application Data

(60) Provisional application No. 63/318,976, filed on Mar. 11, 2022.

(51) Int. Cl.
  *G01N 33/28* (2006.01)
  *E21B 49/08* (2006.01)
  (Continued)

(52) U.S. Cl.
  CPC ......... *G01N 33/2823* (2013.01); *E21B 49/08* (2013.01); *G01V 20/00* (2024.01); *G06N 3/08* (2013.01); *E21B 2200/20* (2020.05)

(58) Field of Classification Search
  None
  See application file for complete search history.

(56) References Cited

U.S. PATENT DOCUMENTS 6,350,986 B1 * 2/2002 Mullins ................. E21B 49/088
                                                           250/269.1
6,661,226 B1 * 12/2003 Hou ...................... G01N 24/081
                                                           324/303

(Continued)

FOREIGN PATENT DOCUMENTS

WO          2022/031533          2/2022

OTHER PUBLICATIONS

Kallenbasti et al., "Data Driven Model for Contamination Estimation and Monitoring Method to Optimize Fluid Sampling," SPE International Society of Petroleum Engineers, Nov. 9, 2020, SPE-203325-MS, 15 pages.

(Continued)

*Primary Examiner* — Lina Cordero
(74) *Attorney, Agent, or Firm* — Hogan Lovells US LLP

(57) ABSTRACT

A system and method for determining reservoir fluid contamination of a reservoir is disclosed. The system includes one or more sensors to detect field measures from reservoir fluid of the reservoir and includes memory and at least one processor to execute instructions from the memory to cause the system to perform further steps. A step by the at least one processor is to simulate relationship data having purity levels correlated to volumes or times associated with extraction of an applied or simulated fluid for varying modeled rock formations. A further step is to fit one or more of the relationship data to the field measures to generate errors. Yet another step is to determine the reservoir fluid contamination from one of the purity levels that is associated with the relationship data that is within a threshold error value or error range of the errors.

20 Claims, 8 Drawing Sheets

(51) Int. Cl.
    *G01V 20/00*         (2024.01)
    *G06N 3/08*          (2023.01)

(56)         References Cited

U.S. PATENT DOCUMENTS

| | | | |
|---|---|---|---|
| 7,299,136 B2 | 11/2007 | DiFoggio | |
| 7,372,264 B2 | 5/2008 | Akkurt | |
| 8,099,241 B2 * | 1/2012 | Niu | E21B 49/10 |
| | | | 73/152.55 |
| 9,121,263 B2 | 9/2015 | Zazovsky | |
| 10,280,745 B2 | 5/2019 | Eyuboglu | |
| 10,309,885 B2 | 6/2019 | Zuo | |
| 10,316,656 B2 | 6/2019 | Zuo | |
| 10,781,686 B2 | 9/2020 | Wang | |
| 11,021,951 B2 | 6/2021 | Olapade | |
| 2005/0216196 A1 * | 9/2005 | Akkurt | G01N 24/081 |
| | | | 702/6 |
| 2006/0250130 A1 | 11/2006 | Akkurt | |
| 2010/0169020 A1 | 7/2010 | Niu | |
| 2017/0350236 A1 | 12/2017 | Shen | |
| 2019/0106987 A1 * | 4/2019 | Kristensen | E21B 49/084 |
| 2020/0018739 A1 * | 1/2020 | Khan | E21B 49/081 |
| 2020/0257654 A1 | 8/2020 | Chen | |
| 2021/0047924 A1 | 2/2021 | Kallenbasti | |
| 2021/0054738 A1 | 2/2021 | Dai | |
| 2022/0034224 A1 | 2/2022 | Hunnur | |

OTHER PUBLICATIONS

Kristensen et al., "Real-Time Formation Evaluation and Contamination Prediction Through Inversion of Downhole Fluid-Sampling Measurements," May 2019 SPE Reservoir Evaluation & Engineering, 17 pages.

International Search Report and Written Opinion mailed Jun. 7, 2023 in corresponding PCT Application No. PCT/US2023/014901.

Katende et al., "Experimental quantification of the effect of oil based drilling fluid contamination on properties of wellbore cement," Journal of Natural Gas Science and Engineering, Jul. 2020, vol. 79, 15 pages.

* cited by examiner

200

210  204  212  202

208  214  206

300

302

306  308

Modelling System 318

Extractor 316

304

Injector 314  310  312

SYSTEM AND METHOD FOR ESTIMATING RESERVOIR FLUID CONTAMINATION

CROSS-REFERENCES TO RELATED APPLICATIONS

This application is related to and claims the benefit of priority from U.S. Provisional Application 63/318,976, titled SYSTEM AND METHOD FOR ESTIMATING RESERVOIR FLUID CONTAMINATION, filed Mar. 11, 2022, the entire disclosure of which is incorporated by reference herein for all intents and purposes.

BACKGROUND

1. Field of Invention

This invention relates in general to equipment used in the natural gas industry, and in particular, to estimating reservoir fluid contamination using machine learning that incorporates simulation measures correlated to field measures for a reservoir.

2. Description of the Prior Art

A drilling well is a structure formed in subterranean or underwater geologic structures, or layers, also referred to as formations that constitute a reservoir. Such subterranean or underwater geologic structures or layers incorporate reservoir fluids (such as liquids, gases, or a combination thereof) that are extracted from a drill site or a well site (such as a wellbore). Wireline logging tools may be used with capability to estimate reservoir fluid contamination levels. An understanding of a reservoir fluid contamination level, in real time, requires collecting a clean sample and performing analysis on such a sample, where the analysis is a feature that is user-dependent and may not be reproducible.

SUMMARY

In at least one embodiment, a system for determining reservoir fluid contamination for a reservoir is disclosed. The system includes one or more sensors to detect field measures from reservoir fluid of the reservoir. The system also includes a memory and at least one processor to execute instructions from the memory. In at least one embodiment, the instructions cause the system to perform functions, including to simulate a plurality of relationship data that include a plurality of purity levels correlated to a plurality of volumes or times associated with extraction of an applied or simulated fluid for varying modeled rock formations. A further function is to fit one or more of the plurality of relationship data to the field measures to generate a plurality of errors. Yet another function is to determine the reservoir fluid contamination from at least one of the plurality of purity levels that is associated with the one or more of the plurality of relationship data that is within a threshold error value or error range of the plurality of errors.

In at least one embodiment, a method for determining reservoir fluid contamination for a reservoir is also disclosed. The method includes detecting, using one or more sensors, field measures from reservoir fluid of the reservoir. The method also includes simulating, using at least one processor, a plurality of relationship data that include a plurality of purity levels correlated to a plurality of volumes or times associated with extraction of an applied or simulated fluid for varying modeled rock formations. A further step of the method is to fit one or more of the plurality of relationship data to the field measures to generate a plurality of errors. Yet another step of the method is to determine the reservoir fluid contamination from at least one of the plurality of purity levels that is associated with the one or more of the plurality of relationship data that is within a threshold error value or error range of the plurality of errors.

BRIEF DESCRIPTION OF THE DRAWINGS

Various embodiments in accordance with the present disclosure will be described with reference to the drawings, in which.

DETAILED DESCRIPTION

Figure 1:
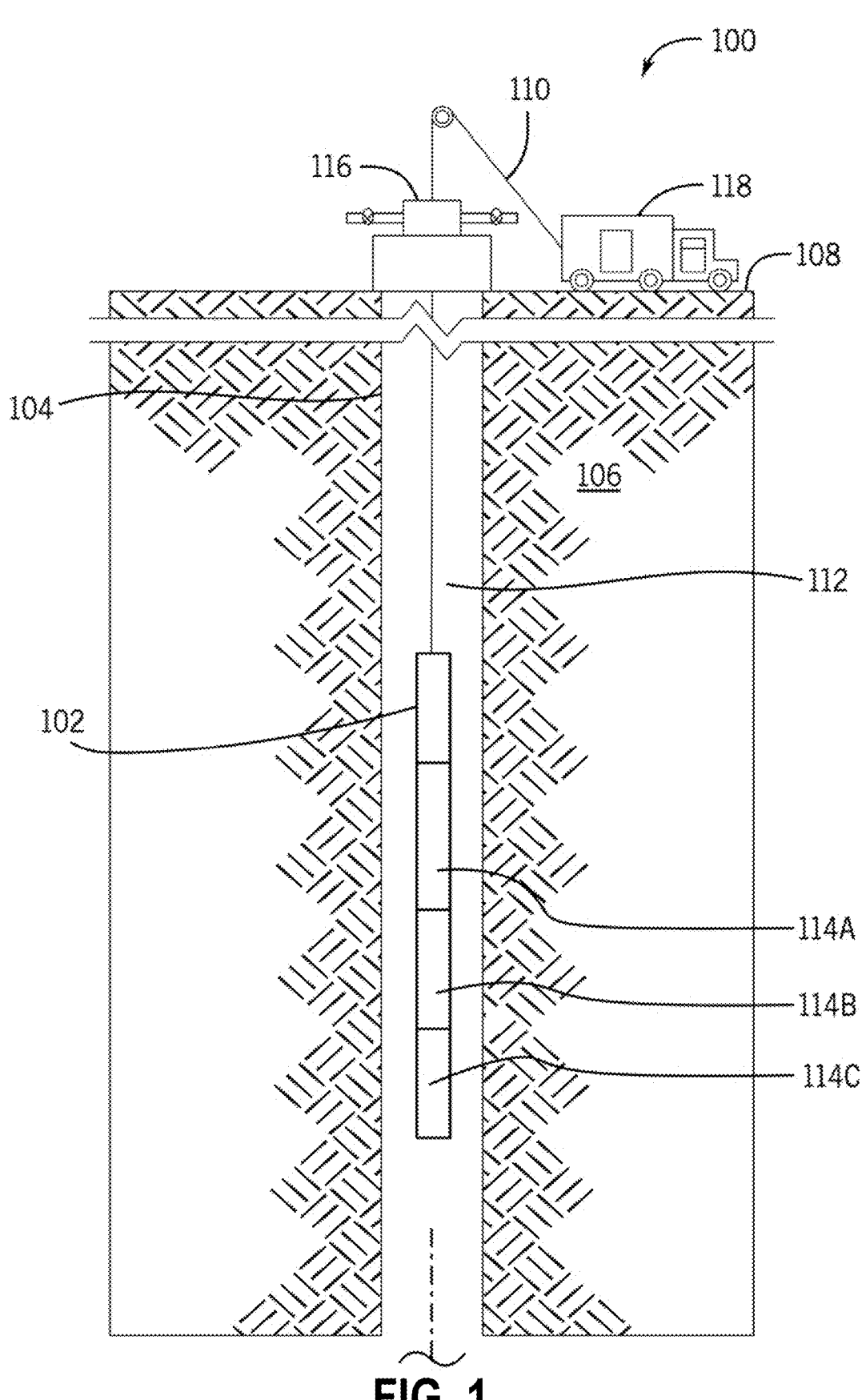
FIG. 1 illustrates an example environment subject to improvements of at least one embodiment herein.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described. Various other functions can be implemented within the various embodiments as well as discussed and suggested elsewhere herein. In at least an aspect, the present disclosure is to a system and a method for determining reservoir fluid contamination for a reservoir to address one or more deficiencies noted above.

The system and method herein generate information, such as fit and error, between field measurements from sensors applied to a reservoir fluid of a reservoir and a number of relationship data having purity levels correlated to volumes or times associated with extraction of an applied or simulated fluid for varying modeled rock formations. A determination of a reservoir fluid contamination can be made from at least one of the purity levels that is associated with the one or more of the relationship data that is within a threshold error value or error range of the errors, for example.

In at least one embodiment, the relationship data is a simulation that includes a fluid sampling to achieve a fluid sample that is representative of reservoir fluid from a reservoir. As a result of invasion of drilling fluid, used during pumping out of reservoir fluid, such reservoir fluid may be contaminated. The contamination may decrease (or purity levels increase) with respect to reservoir fluid as more reservoir fluid is pumped out, which also removes more of the drilling fluid.

In at least one embodiment, there may be uncertainty with respect to contamination (or purity levels) in relation to an amount of fluid being extracted. The amount of fluid being extracted may be given by a volume at different times of such extraction when such a volume is consistently maintained for a time of the extraction. In at least one embodiment, such uncertainty may be addressed by the system and method herein for determining reservoir fluid contamination for a reservoir.

In at least one embodiment, the method and system herein use a machine learning algorithm, such as one or more neural networks, along with simulated relationship data having purity levels correlated to different volumes or times associated with extraction of an applied or simulated fluid for varying modeled rock formations, and with field measures detected by one or more sensors for reservoir fluid of a reservoir. Further, the different volumes may be associated with different times to replicate the change in contamination levels over time.

In at least one embodiment, a machine learning algorithm, as including one or more neural networks, is adapted to perform and learn from a large number of simulations, which generates relationship data. The relationship data may be visualized as curves of purity levels (or contamination) against volume in liters (also taken in reference to different times) of simulated or applied fluid through modeled rock formations. In at least one embodiment, such modeled rock formations may be 3-dimensional (3D) modelled rock simulations of a formation. The modeled rock formations may be an individual physical rock formation that is injected with contaminant and created as part of one or more physical rock formations from the modeled rock formations. Different purity levels are determined by a volume of extracted applied fluid through the one or more physical rock formations.

In at least one embodiment, simulated relationship data may be used with field measures to find a best series of relationship data to match the field measures. The best series or matches may be used for prediction of contamination in future volumes of extracted reservoir fluid from the reservoir or can be used to predict new contamination in a new reservoir. In at least one embodiment, the machine learning algorithm is able to train one or more neural networks using at least the relationship data and the errors obtained between the relationship data and the field measures, in a feedback loop, for instance. In at least one embodiment, such a trained machine learning algorithm, including a trained neural network, can be used to infer a reservoir fluid contamination for a new reservoir based in part on new field measures tested with the trained one or more neural networks for a same or a new reservoir.

In at least one embodiment, field measures taken from one or more sensors are proven to show a behavior that may be analogous to a shape of purity levels (or contamination) curve resulting from simulated modeling performed in the system or method described herein. A hypothesis used in the machine learning algorithm includes that a linear or other correlation exists between a purity level and time (and volume) curves from a simulation taken against field measures obtained from one or more fluid properties (against a time and a volume) of a reservoir fluid, during a reservoir operation. A loss function associated with such a correlation can enable learning of the purity level inferred for a volume or time associated with a reservoir using the field measures. As such, fluid properties for field measures, including optical measures, sound speed measures, refractive index measures, density measures, and viscosity measures, can be used with relationship data from simulations associated with a plurality of reservoir fluid contamination to determine a reservoir fluid contamination specific to the reservoir or a volume or time at which one of the field measures is obtained.

In at least one embodiment, a best set of simulations that fit field measures is determined. Such a best set of simulations may be used in calibrations or used for forecasting of contamination or purity level for new reservoirs or for future extractions of an existing reservoir used for providing such field measures. The forecasting of contamination or purity level provides economic value at least in field operations by reducing associated uncertainties as discussed elsewhere herein. An issue overcome is of subjectiveness of trying to find a best fit and specific linear function to provide a cost function between field measures (which can be represented in field measure curves and simulated relationship data). In at least one embodiment, at least partial field measures that can be used to provide a best fit for a linear function may be realized by minimizing an error between the simulation relationship data and the field measures.

In at least one embodiment, FIG. 1 illustrates an example environment 100 subject to improvements described herein. A system, such as for determining reservoir fluid contamination for a reservoir may be supported by other subsystems, including by one or more downhole and/or platform-based tools 102. A platform-based tool may be above terrain surface 108 (of terrain 106) or above water surface. A downhole and/or platform-based tool 102 may be part of a string 112 of tools, which may include other components utilized for wellbore operations.

In at least one embodiment, a string 112 may include other tools 114A-114C than components or an entire system for determining reservoir fluid contamination for a reservoir. The tools may be part of sensors, measurement devices, communication devices, and the like. Further, a string 112 may include one or more tools to enable at least one of a logging operation (such as wireline logging), a perforating operation, a pressure testing, a reservoir fluid sampling, or a well intervention. In at least one embodiment, nuclear logging tools, fluid sampling tools, and core sampling devices may be also used in a string 112. The one or more tools may include part of or a complete subsystem to perform functions described throughout herein.

In at least one embodiment, perforating operations may include ballistic devices being lowered into a wellbore 104 to perforate casing or the formation. In at least one embodiment, well interventions may include operations relating to analysis of one or more features of a wellbore 104, followed by performing one or more tasks in response to at least one feature. One or more of such features may include data acquisition, cutting, and cleaning. As such, in at least one embodiment, a string 112 may refer to a combination of one or more tools lowered into a wellbore 104. In addition, passive devices may also be included, such as centralizers or stabilizers, and tractors may be provided to facilitate movement of a string 112.

In at least one embodiment, power and/or data conducting tools may be used to send and receive signals and/or electrical power. Sensors may be incorporated into various components of a string 112 and may be enabled to communicate with a surface (platform) or with other string components. In an example, such communication may be via a cable 110, via mud pulse telemetry, via wireless communications, and via wired drill pipe, in a non-limiting manner. In at least one embodiment, it should be appreciated that while embodiments may include a wireline system, a rigid drill pipe, coiled tubing, or any other downhole exploration and production methods may be utilized with at least one embodiment herein.

In at least one embodiment, an environment 100 includes a wellhead assembly 116 shown at an opening of a wellbore 104 to provide pressure control of a wellbore and to allow for passage of equipment into a wellbore 104. The equipment may include a cable 110 and a string 112 of tools. A cable 110 is or may include a wireline that is spooled from a service truck 118. The cable 110 may extend to an end of a string 112. Further, during operation, a cable 110 may be provided with some slack as a string 112 is lowered into a wellbore 104 to a predetermined depth.

In at least one embodiment, fluid may be delivered into a wellbore 104 to drive or assist in movement of a string 112. This may be a case where gravity may not be sufficient to assist, such as in a deviated wellbore. A fluid pumping system may be provided at a surface 108 to pump fluid from a source into a wellbore 104 via a supply line or conduit. Further, control of a rate of travel of a downhole assembly and/or control of tension on a wireline 110 may be provided by a winch on a surface 108. The winch system may be part of a service tuck 118. In addition, a combination of fluid flow rate and tension on a wireline 110 can contribute to a travel rate or rate of penetration of a string 112 into a wellbore 104.

In at least one embodiment, a provided cable 110 may be an armored cable that includes conductors for supplying electrical energy (power) to downhole devices and communication links for providing two-way communication between a downhole tool and surface devices. Further, tools such as tractors, may be disposed along a string 112 to facilitate movement of such a string 112 into a wellbore 104. A string 112 may be retrieved from a wellbore 104 by reeling a provided cable 110 upwards using such a service truck 118. In at least one embodiment, logging operations may be performed as a string 112 is brought to a surface 108.

A system of a downhole tool 102 herein can include a wireline system for determining reservoir fluid contamination for a reservoir, where the system is partly in a downhole environment and partly on the surface. In at least one embodiment, wireline logging tools are able to evaluate a reservoir fluid contamination in a downhole environment of a reservoir or is able to retrieve samples for a surface analysis of such a reservoir.

Figure 2:
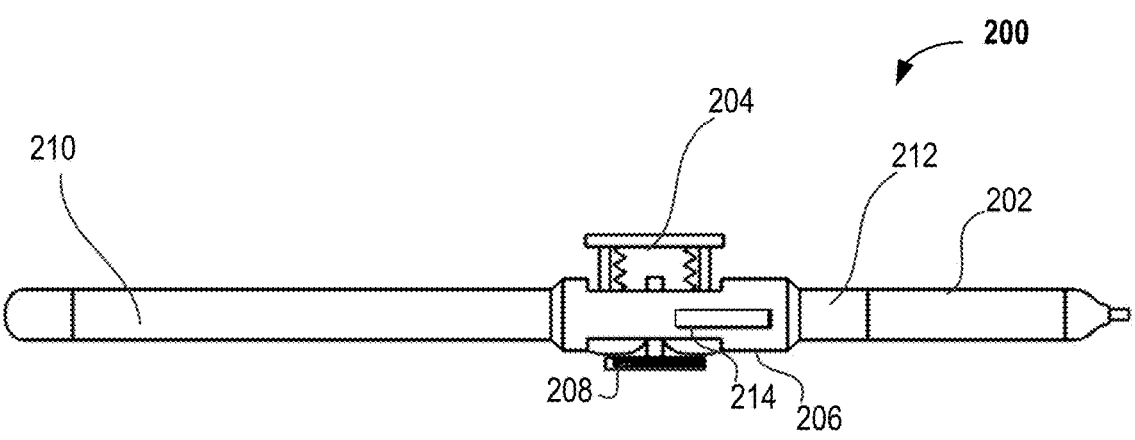
FIG. 2 illustrates a downhole tool that can include a wireline system having one or more sensors for detecting field measures from reservoir fluid of a reservoir or having extraction components for extracting samples of the reservoir fluid, in at least one embodiment.

FIG. 2 illustrates a downhole tool 200 that can include a wireline system 202 for determining reservoir fluid contamination of a reservoir, where the system is partly in the downhole environment and partly on the surface or is fully in the downhole environment. FIG. 2 may be taken as an illustration of a test or downhole tool 200 subject to improvements disclosed herein, in accordance with various embodiments. A downhole tool 200 can include a downhole instrument (which may be part of the platform-based tools 102 describe with respect to FIG. 1) with compartments for one or more sensors 214 and a wireline system 202 for analysis of a reservoir fluid of a reservoir. At least some of these components may be used to collectively provide capability to perform analysis of a reservoir from a downhole application. A wireline system 202 for analysis of a reservoir may be coupled to an above-ground or surface subsystem, such as at least one processor executing instructions from a memory to perform multiple functions, for instance.

FIG. 2 illustrates a downhole tool 200 that can include a wireline system (such as reference 202) for determining reservoir fluid contamination of a reservoir, where the system is partly in the downhole environment and partly on the surface or is fully in the downhole environment. The wireline system 202 may be attached to one end of an armored electrical cable as illustrated in FIG. 1. The wireline system 202 may be lowered into a wellbore that is drilled through the earth.

The cable may be extended into the wellbore by a winch located at the earth's surface. The wireline system 202 may include a back-up shoe and a mechanism for extending the shoe, generally illustrated in reference numeral 204. The shoe and associated mechanism may be disposed within a housing 206. The housing 206 may include a tubular probe 208 which may be selectively extended and put into contact with a wall of a wellbore. A sample tank 210 can be attached to a lower end of the housing 206 and can be selectively hydraulically connected to the probe 208 in order to store samples of fluids withdrawn from the reservoir.

The probe 208, the shoe and associated mechanism 204, and selective valves may be disposed within the housing 206 for operating the probe 208 and for operating the shoe and associated mechanism 204. The downhole tool 200 can receive hydraulic operating power from a hydraulic power unit 212 attached to an upper end of the housing 206. Various operating functions of the wireline system 202, including extension of the shoe and associated mechanism 204, as well as extension of the probe 208, may be controlled by a system operator using command signals provided to control circuits associated with the downhole tool 200.

The command signals may be decoded in an electronics unit/processor disposed within the housing 206. The wireline system 202 includes sensors 214 in the housing 206 for detecting field measures from reservoir fluid of the reservoir, such as reservoir fluid collected in the sample tank 210. Measurements from the sensors may be transmitted to the earth's surface as electrical signals generated by an electronics unit/processor within the housing 206. At the earth's surface the signals are decoded by a signal processor which is also electrically connected to the cable. The decoded signals are reformatted into measurements which can be observed by the system operator and can be recorded by a recorder connected to the signal processor. Electronics unit/processor of the housing 206 performs the simulations, fitting, and determinations discussed herein that are associated with reservoir fluid contamination from at least one of the plurality of purity levels that is associated with the one or more of the plurality of relationship data that is simulated and that is within a threshold error value or error range of the plurality of errors.

As the downhole tool 200 is lowered into the wellbore, the depth at which the downhole tool 200 is located may be indicated by a depth indicator which may be in contact with the cable used to lower the downhole tool 200. The depth indicator can measure amounts of cable extended into the wellbore. When the downhole tool 200 is determined to be positioned adjacent to a formation of interest, a system operator enters commands into the control circuits to lock the downhole tool 200 in position by extending the back-up shoe and associated mechanism 204. The probe 208 may be extended and withdrawal of a fluid sample can be initiated. As such, a wireline system 202 of a downhole tool 200 may be a subsystem that works with the above-ground or surface subsystem.

Figure 3:
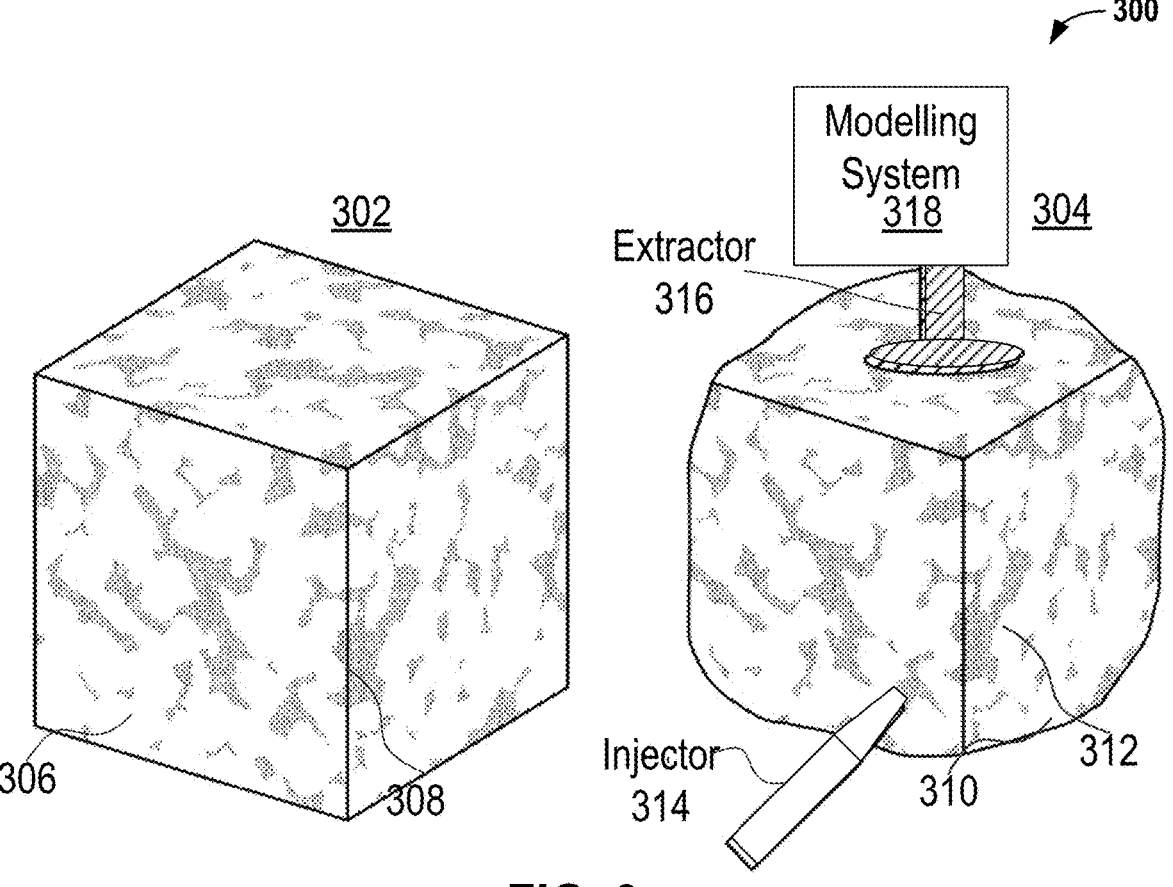
FIG. 3 illustrates varying modeled rock formations to support simulation of a plurality of relationship data having a plurality of purity levels correlated to a plurality of volumes or times of applied fluid extracted through such modeled rock formations, in at least one embodiment.

FIG. 3 illustrates varying modeled rock formations 300 to support simulation of a plurality of relationship data having purity levels correlated to a volumes (at different times) of applied fluid extracted through such modeled rock formations 300, in at least one embodiment. In FIG. 3, a first modeled rock formation 302 may be generated to include a network of void or pore structure 308 and solid structure 306, using one or more images of a physical rock formation and using physical variables.

In at least one embodiment, the physical variable includes input data having one or more of a simulated formation pressure, a simulated formation porosity, a simulated formation permeability, a simulated formation flow rate, a simulated invasion parameter, a simulated anisotropy ratio, and simulated packers. In at least one embodiment, the input data may be randomized based on part on a sample of physical rocks obtained from a reservoir using a downhole tool 200.

The modeled rock formations 302 may be, therefore, a simulated 3D mesh structure generated using such input data and is able to provide information associated with how a simulated fluid would behave through a 3D mesh structure. As such, it is possible to simulate purity measures and volume measures (and different times of extraction) for the modeled rock formation 302. The purity measures and the volume measures are then provided as part of the relationship data to be used for fitting with field measures of a reservoir fluid from a reservoir. As such, the modeled rock formation 302 illustrated in FIG. 3 remains a computer-based model.

In at least one embodiment, a second modeled rock formation 304 is one or more physical rock formations generated from a computer-based model. In at least one embodiment, one or more physical rock formations may be generated using a 3D printer or other tool. In at least one embodiment, the physical rock formation 304 may be generated by randomized input data provided to a computer-based model or images initially provided on a computer.

In at least one embodiment, a contaminant can be injected, using an injector 314, into an individual physical rock formation 304. The applied fluid may be extracted, through the individual physical rock formation 304, using an extractor 316. A modeling system 318 may be used to analyze the contaminants in the extracted applied fluid to provide purity measures and volume measures (at different times) that may be provided as part of the relationship data to be used for fitting with field measures of a reservoir fluid from a reservoir. Therefore, determining a purity level for the fitting operation herein may be based in part on the extracted applied fluid.

In at least one embodiment, a network of void or pore structure 308, 312 exists in simulated or physical structure 306, 310 of a modeled rock formation 302, 304 may include connected voids or pores and can also include isolated voids or pores. As such, when pores are isolated from a network that is otherwise between void or pore structure 308, 312, in a modeled rock formation 302, 304, there may be changes in contamination and travel of simulated or applied fluid therethrough. In at least one embodiment, this feature allows modeling of the modeled rock formations 302, 304 having a simulated permeability, a simulated porosity, and a simulated flow rate for applied fluid through the modeled rock formation 302, 304.

Figure 4A:
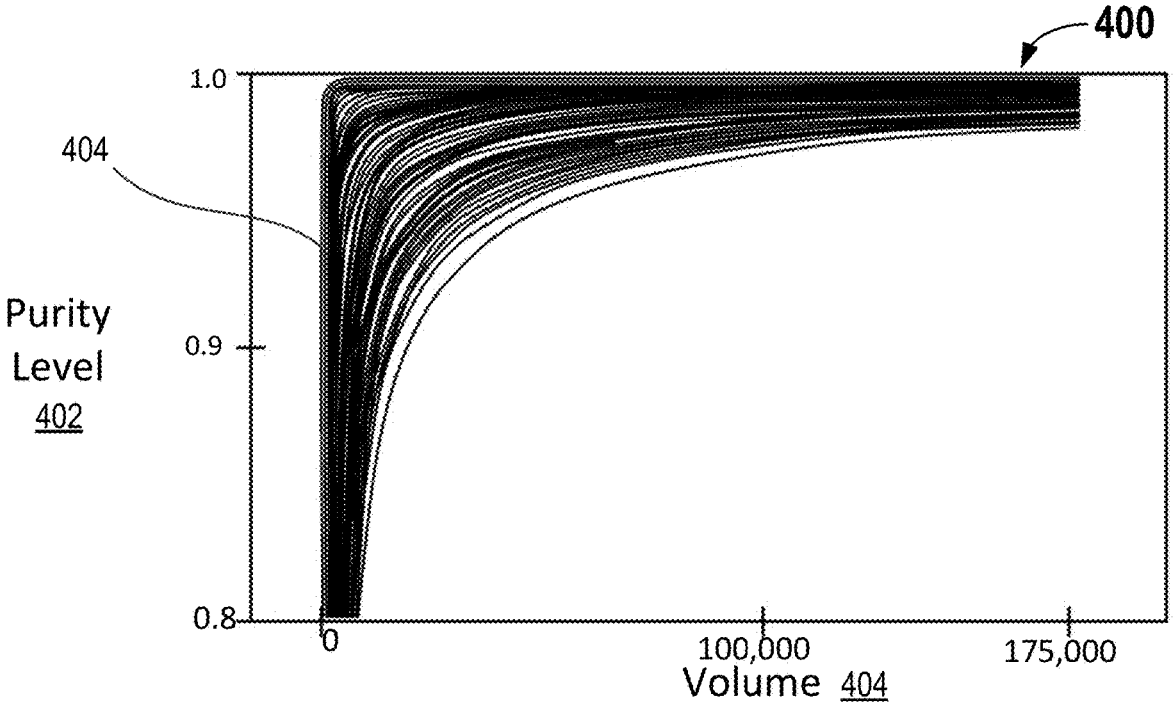
FIG. 4A illustrates simulated relationship data having a plurality of purity levels correlated to a plurality of volumes of applied fluid for varying modeled rock formations, according to at least one embodiment.

FIG. 4A illustrates simulated relationship data 400 having a plurality of purity levels 402 correlated to a plurality of volumes 404 (at different times) of applied fluid for varying modeled rock formations, according to at least one embodiment. The simulated relationship data 400 is visualized as a collection of simulation curves generated from modeled rock formations 302, 304. The simulated relationship data 400 includes results of fluid contamination (purity level) 402 versus time and/or volume 404 for a wide range of reservoir and fluid properties that are represented in the input data for different modeled rock formations 302, 304. Further, the input data covers a wide range of variables, such a permeability, invasion, anisotropy ratio, or different packers, but are not limited to these factors.

Figure 4B:
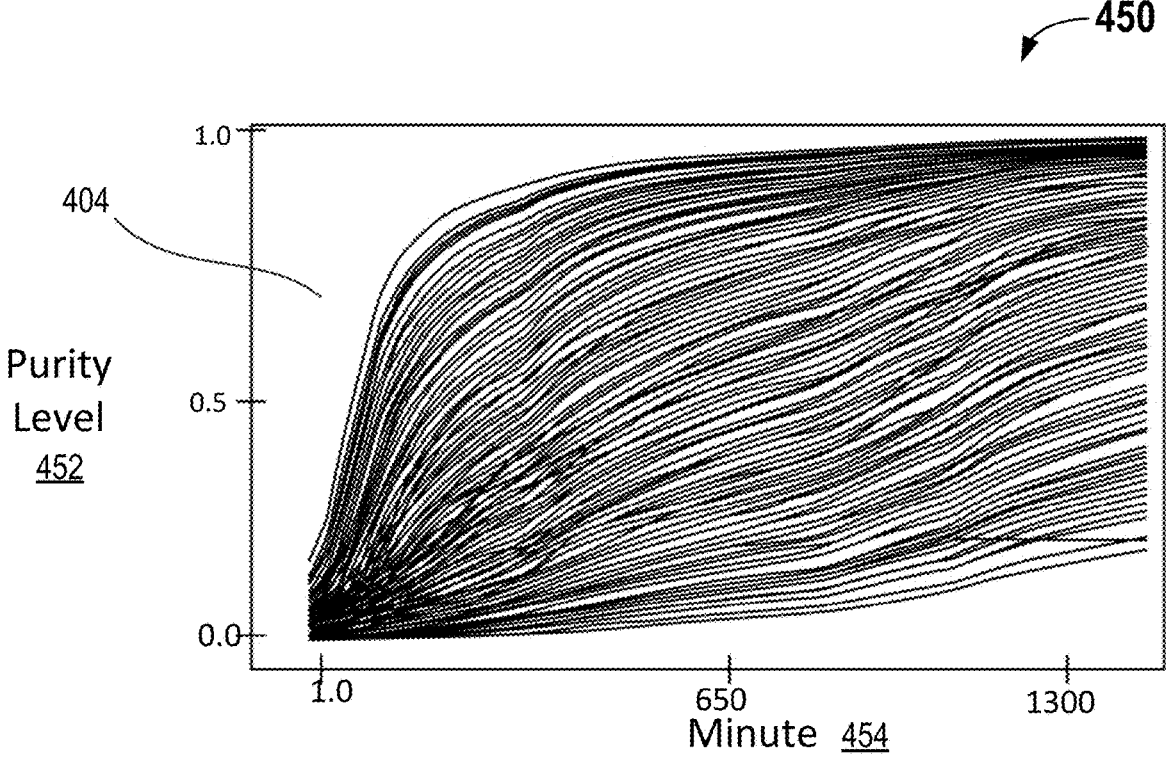
FIG. 4B illustrates simulated relationship data having a plurality of purity levels correlated to a plurality of times over which applied fluid is collected or sampled for varying modeled rock formations, according to at least one embodiment.

FIG. 4B illustrates simulated relationship data 450 having a plurality of purity levels 452 correlated to a plurality of times 454 over which applied fluid for varying modeled rock formations is collected or sampled, according to at least one embodiment. In at least one embodiment, the simulated relationship data 450 is visualized as a collection of simulation curves generated from modeled rock formations 302, 304. The simulated relationship data 450 includes results of fluid contamination (purity level) 452 versus time and/or volume 454 for a wide range of reservoir and fluid properties that are represented in the input data for different modeled rock formations 302, 304. In at least one embodiment, the input data covers a wide range of variables, such a permeability, invasion, anisotropy ratio, and different packers, but are not limited to these factors. Further, such relationship data 400 may be used with the field measures in a plot as illustrated in at least FIGS. 5D-6A.

Figures 5A, 5B:
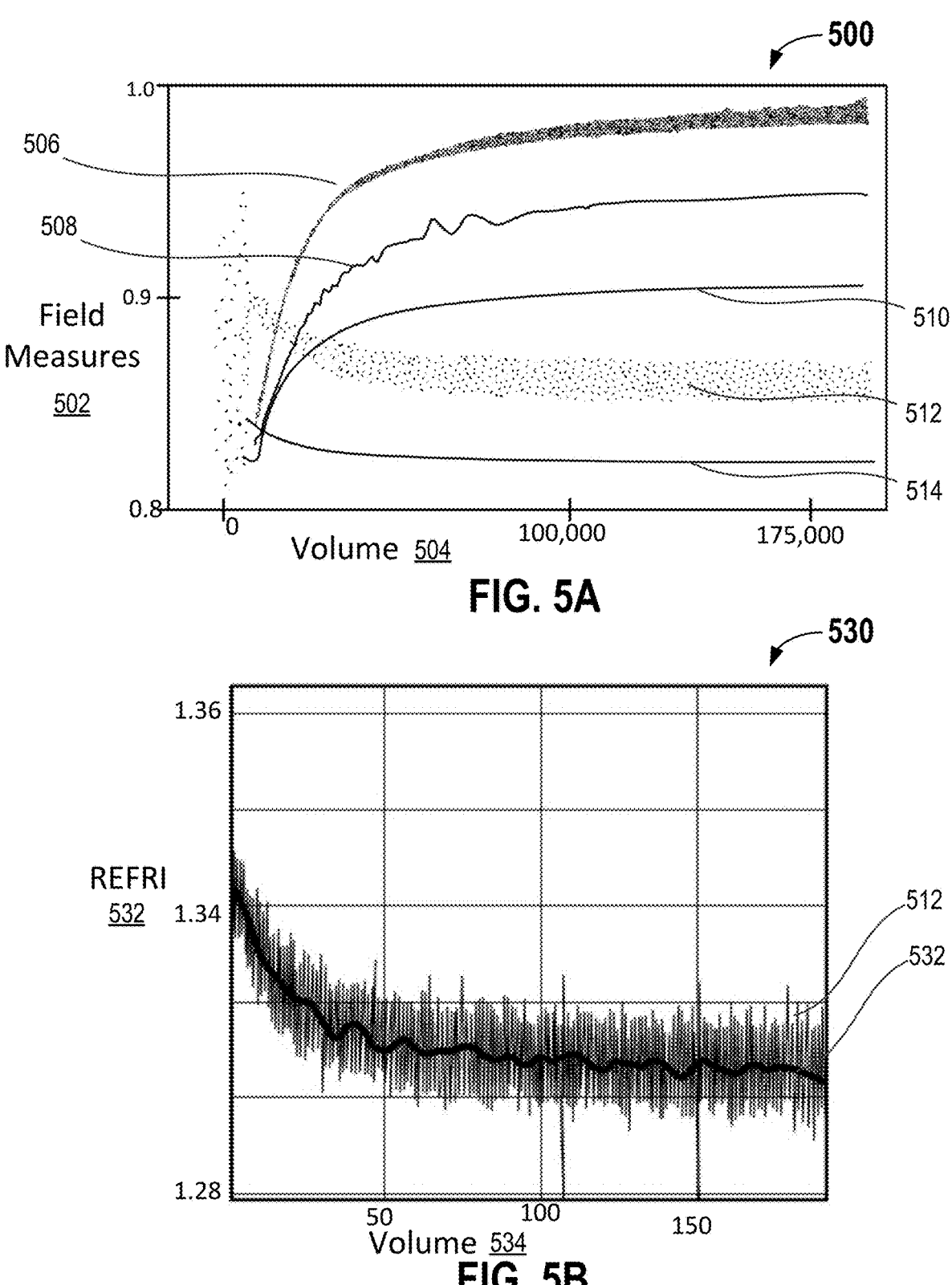
FIG. 5A illustrates field measures to be used with simulated relationship data to generate errors as described herein, according to at least one embodiment.
FIG. 5B illustrates a plot one type of field measures with smoothening applied and to be used with simulated relationship data to generate errors as described herein, according to at least one embodiment.

FIG. 5A illustrates field measures 500 to be used with simulated relationship data 400 to generate errors as described herein, according to at least one embodiment. In at least one embodiment, a system and method herein enable fitting of relationship data 400 to the field measures 500 to find errors in such a fitting operation. In at least one embodiment, a combination of the field measures 500 and simulated relationship data can be used to predict purity levels (contamination) versus time/volume for future reservoirs and for current reservoirs having ongoing extractions.

In at least one embodiment, machine learning algorithms incorporating one or more neural networks may be used to identify one or more simulated relationship data 400 that are analogues or a best fit to the field measures 500. This may be by a feedback network or feedforward propagation of errors identified during the fitting operation for at least part of some field measures 500 used with the simulated relationship data 400.

In at least one embodiment, the field measures 500 include different types of field measures, such as absorbance measures (such as a difference between an absorbance measure OD3 and an absorbance measure OD5) 506, SSDT (Slowness in Sound Speed or an inverse of Sound Speed) measures 508, further absorbance measures (such as differences in absorbance measures OD4 and OD6) 510, REFRI (Refractive Index of the Fluid) measures 512, and TFDEN (Fluid Density) measures 514.

In at least one embodiment, before performing a fitting operation as described in the system and method herein, a smoothening operation may be performed. The smoothening operation includes applying a smoothening algorithm to the field measures 500 to generate a smoothened version of the field measures 500. An outlier detection and removal operation may be performed with the smoothening algorithm for the field measures. The smoothened version may be a mean curve through as many datapoints of the field measures 500 for at least each of the field measures that are sparse data (such as measures 506, 512). Further, the smoothening algorithm with any further operation may be used to generate a smoothened version of the field measures. An individual set of the smoothened version of the field measures may be used with an individual set of the plurality of relationship data 400 to identify a linear match. The linear match may be used in part to generate the plurality of errors.

FIG. 5B illustrates a plot 530 of one type of field measures 500 with smoothening applied and to be used with simulated relationship data to generate errors as described herein, according to at least one embodiment. For example, one type of the field measures may be REFRI 512 that is plotted against volume 534. The smoothening includes applying a smoothening algorithm to the REFRI 512 field measures to generate a smoothened version 532 of the REFRI 512 field measures. The smoothened version 532 may be one or more mean curves through as many datapoints of the REFRI 512 field measures. An individual set of the smoothened version 532 of the REFRI 512 field measures may be used with an individual set of the plurality of relationship data 400 (and as illustrated with respect to FIGS. 5D, 5E) to determine a linear match. The linear match may be used in part to generate the plurality of errors as detailed further with respect to at least FIGS. 5C-6B herein.

Figures 5C, 5D, 5E:
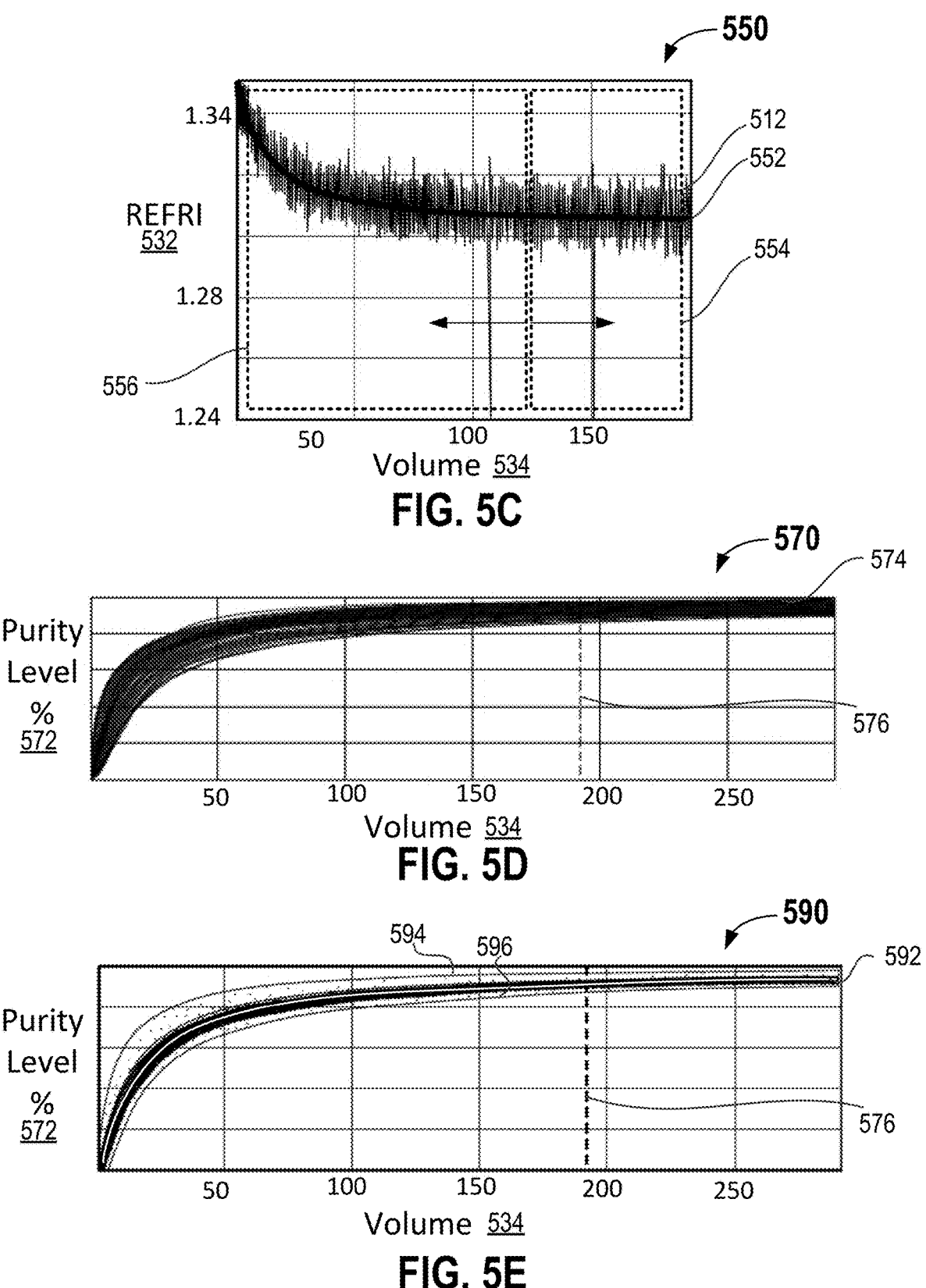
FIG. 5C illustrates a plot the one type of field measures with one or more best fit lines applied and to be used with simulated relationship data to generate errors as described herein, according to at least one embodiment.
FIG. 5D illustrates a plot of best-matched simulated relationship data against field measures using a plurality of purity levels correlated to a plurality of volumes, according to at least one embodiment.
FIG. 5E illustrates a plot of a spread of the best-matched simulated relationship data against field measures using a plurality of purity levels correlated to a plurality of volumes, according to at least one embodiment.

FIG. 5C illustrates a plot 550 of the one type of field measures with one or more best fit lines 552 applied and to be used with simulated relationship data to generate errors as described herein, according to at least one embodiment. In at least one embodiment, the type of field measures is REFRI 552 field measures. Curve fitting (including a nonlinear regression) may be performed for one or more regression differential curves, also referred to as best fit lines 552, to provide best fit of the REFRI 512 field measures that may be translated to one or more nonlinear equations. In an example, however, one or more such best fit lines 552 may be an exponential curve represented in a logarithmic axis as a linear fit. Further, in FIG. 5C, a training set 556 is marked and is distinct from a testing set 554 for use with a machine learning algorithm, such as one or more neural networks. The training set, along with simulated relationship data having purity levels correlated to different volumes or times, may be used to perform testing, and may be used to determine the reservoir fluid contamination based in part on a threshold error value or error range of the plurality of errors from the curve fitting performed.

FIG. 5D illustrates a plot 570 best-matched simulated relationship data against field measures using a plurality of purity levels correlated to a plurality of volumes, according to at least one embodiment. For example, the REFRI 512 field measures, along with SSDR and TEDFN field measures, based in part on their respective best fit lines (such as a best ft line 552), are plotted. The field measures are proven to show a behavior that may be analogous to a shape of purity levels (or contamination) curve resulting from simulated modeling. While illustrated as a collection of lines 574 in FIG. 5D, there may be multiple best fit lines 552 from different field measures provided with the purity level (or contamination) curve resulting from simulated modeling.

Further, in FIG. 5D, at each volume point 576, relevant purity levels 572 may be associated with one or more of the best fit lines 574 provided. This information can be used with a machine learning algorithm that can therefore include a goal of a linear or other correlation existing between a purity level and time (and volume) curves 574 from a simulation taken against field measures obtained from one or more fluid properties (against a time and a volume) of a reservoir fluid, during a reservoir operation.

FIG. 5E illustrates a plot 590 of a spread of the best-matched simulated relationship data against field measures using a plurality of purity levels correlated to a plurality of volumes, according to at least one embodiment. For example, for one of the best fit lines 574, it is possible to determine at least a spread, such as an upper boundary 594 and a lower boundary 596 for each best fit line 592 (corresponding to a best fit line 552 in FIG. 5C, for example) at each volume point 576. The best fit line 592 highlighted may be a mean or other statistical measure associated with the spread.

Figure 6A:
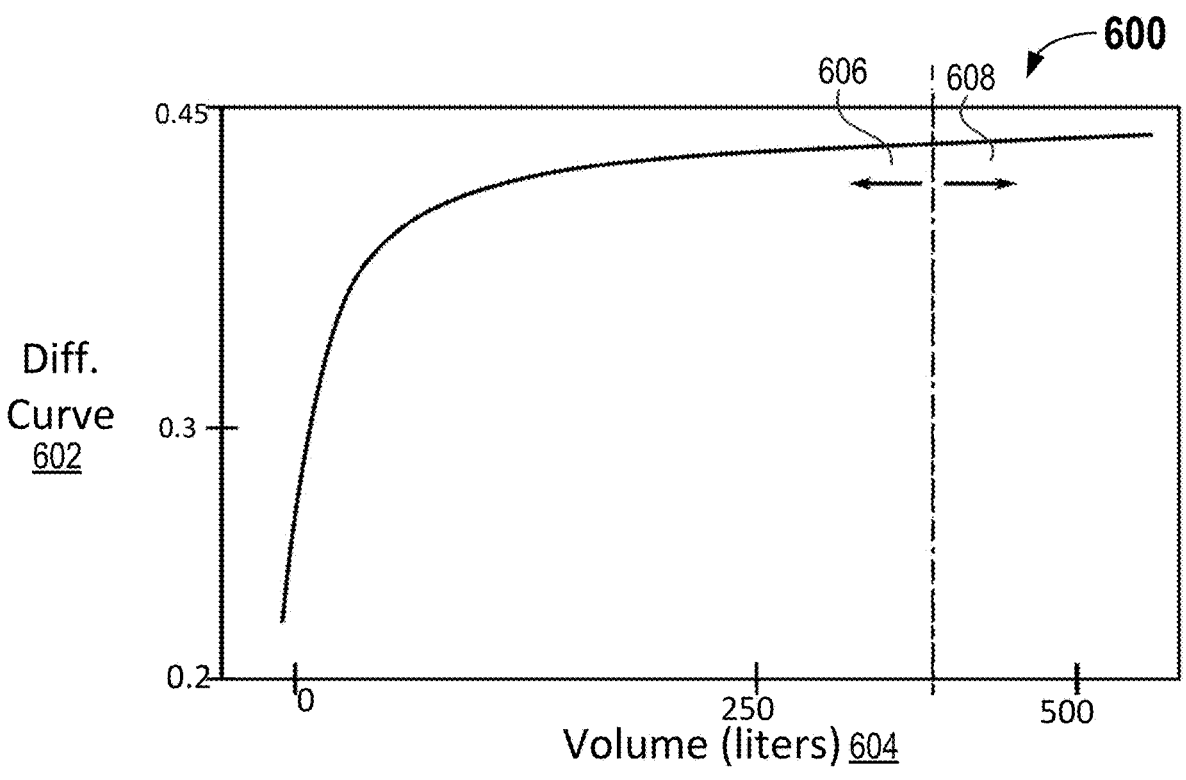
FIG. 6A illustrates a regression differential curve generated as part of the errors from the fitting of simulated relationship data and field measures as described herein, according to at least one embodiment.

FIG. 6A illustrates a regression differential curve 600 generated as part of the errors from the fitting of simulated relationship data and field measures as described herein, according to at least one embodiment. The regression differential curve 600 in FIG. 6A may therefore correspond to one best fit line 592 of FIG. 5E. In at least one embodiment, a regression differential curve 600 illustrates an example of a best fit between the simulated relationship data 400 and the field measures 500 that may be translated to a linear match. For example, once one or more curves fit between the simulated relationship data 400 and the field measures 500, the exponential curve 600 may be represented in a logarithmic axis as a linear match between a purity level of the simulated relationship data 400 that is a best fit in the regression differential curve 600 and a field measure, such as one of differences in absorbance (OD3, OD6) measures 506, 510; SSDT measures 508; REFRI measures 512; and TFDEN measures 514.

Figure 6B:
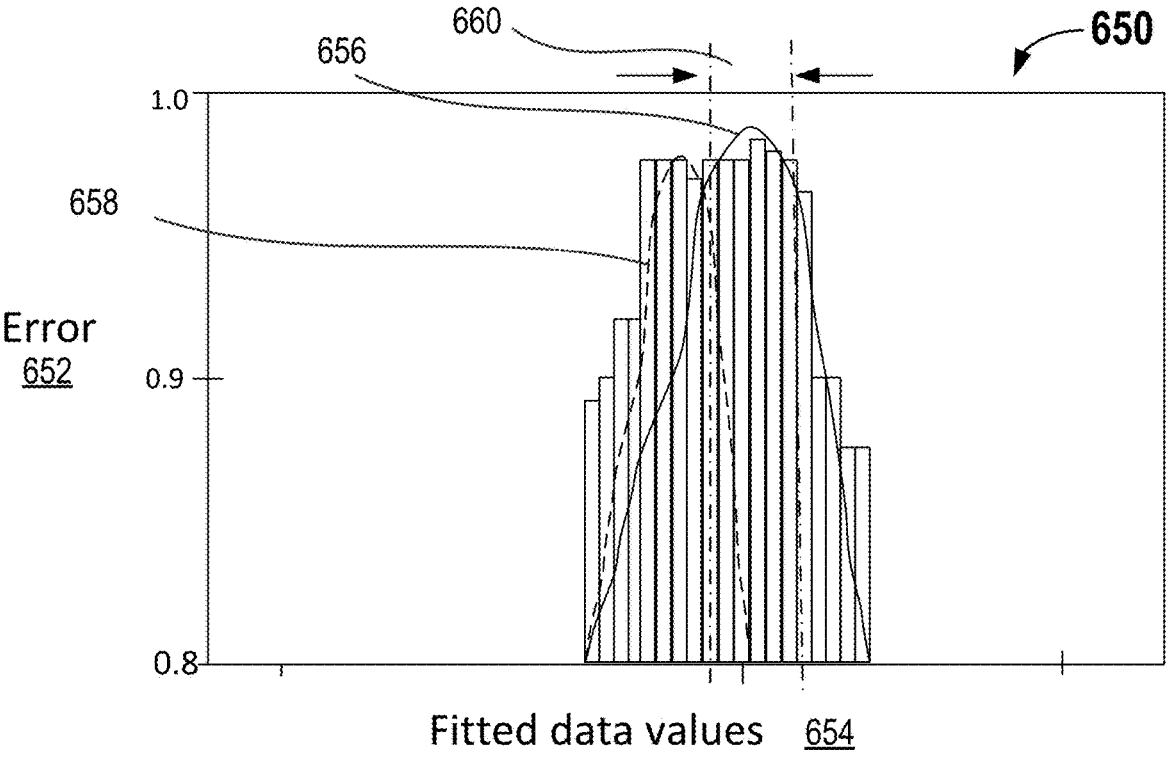
FIG. 6B illustrates a plot of errors that include a threshold error value or error range determined for fitting of simulated relationship data and field measures as described herein, according to at least one embodiment.

FIG. 6B illustrates a plot 650 of errors 652 that include a threshold error value or error range 660 determined for fitting of simulated relationship data 400 and field measures 500 as described herein, according to at least one embodiment. In at least one embodiment, a minimum amount of field measures may be defined for the system and method for determining reservoir fluid contamination for a reservoir.

In at least one embodiment, a linear function transformation is performed, as described with respect to FIGS. 3-5, to match field measures with simulated relationship data. In at least one embodiment, machine learning algorithm may be enabled using one or more neural networks. A hypothesis may be defined for the machine learning algorithm. The hypothesis may be based in part on a shape of the field measures to ensure that such field measures match relationship data that are visualized as the simulation curves 404 and the field measures curves 506-514.

In at least one embodiment, therefore, at least field measures initially determined for a reservoir and any matching simulated relationship data may include datapoints incorporating highest contamination levels but can also include decreased contamination levels as time passes and as more reservoir fluid is pumped out of a reservoir. In at least one embodiment, the contamination in the reservoir fluid will decline.

In at least one embodiment, a match or best fit performed between the field measures and the simulated relationship data is obtained by minimizing errors 652 between different datapoints representing fitted data values 654 of the field measures and the simulated relationship data. As a result, a set of simulation relationship data (such as purity level) may be related to one or more field measures by minimizing the errors 652. In particular, the relationship between a purity level and one or more field measures may be a linear function and may be represented as a linear transformation function.

In at least one embodiment, the linear transformation function can be used to project contamination or purity level for data of such related one or more field measures obtained from reservoir fluid of the same or a new reservoir. In the regression differential curve 602, therefore, the values of the regression differential curve 602 in a first area 606 are fitted simulated relationship data, while a second area 608 of the regression differential curve 602 may include values of contamination or purity level projected from associated contamination or purity level in the underlying simulated relationship data of the first area 606.

In at least one embodiment, instead of selecting training data from a first area 606 to determine a quality of a fit using the testing data in second area 608, a random selection may be performed from any part of the regression differential curve 600. Further, a ratio of the field measures as associated with a regression differential curve 600 at a volume point may be selected. For example, some points in the first area 606 may be ignored while some other points in the same area may be used for training. Some different points in the regression differential curve 600 may be used for testing to determine quality of a fit. In at least one embodiment, this is performed because a part of purity levels in the second area 608 may better represent the data than from the first area 606.

Therefore, multiple ones of the best fit curves are plotted according to FIGS. 5D and 5E. Once a fit is determined between the field measures and the simulation relationship data, those best fit curves may be determined to identify their boundaries. At any volume or time point 576, therefore, a plot 650 of errors that include a threshold error value or error range determined for fitting of simulated relationship data and field measures statistics, as in FIG. 6B, may be generated.

In at least one embodiment, a reservoir fluid contamination is determined from at least one of the plurality of purity levels from a simulated relationship data that is associated with one or more of the relationship data that is within a threshold error value or error range 660 of the plurality of errors 652. In at least one embodiment, different probability curves 658, 656 may be used based in part on a bias established for the fitted data.

For example, if one of the provided field measures 506-514 is determined as providing relevant purity level or contamination for initial reservoir fluid tested, then a threshold error value or error range and a probability curve may be selected of the plurality of errors 652 to be used for determining reservoir fluid contamination of future reservoir fluid. The threshold error value or error range and a probability curve may be used with the linear transformation to allow a wider fit of simulated relationship data with field measures.

In at least one embodiment, the plurality of errors 652 is projected to a plot 650 that is a distribution, such as a probability distribution. The threshold error value or the error range 660 may be determined from a mean of a probability distribution. In a further aspect, a volume of the reservoir fluid may be obtained, as a sample, from the reservoir. In at least one embodiment, such a volume may be determined based in part on the volume measures of a reservoir fluid to be used for the modeled simulation rocks. A reservoir fluid contamination is determined for the sample based in part on an extrapolation of the volume 604 (as in the projection data in the area 608 of FIG. 6A) to at least one of the relationship data after applying one of the plurality of errors 652.

In at least one embodiment, while curve fitting techniques may be able to fit part of a sensor response, a system and method herein is able to utilize an entire dataset from one or more sensors. The use of a threshold error value or error range and a probability curve results in preferential variability when a same purity level determination operation is performed on a same sensor response detected by a tool incorporating one or more such sensors but utilized by different operators.

Figure 7:
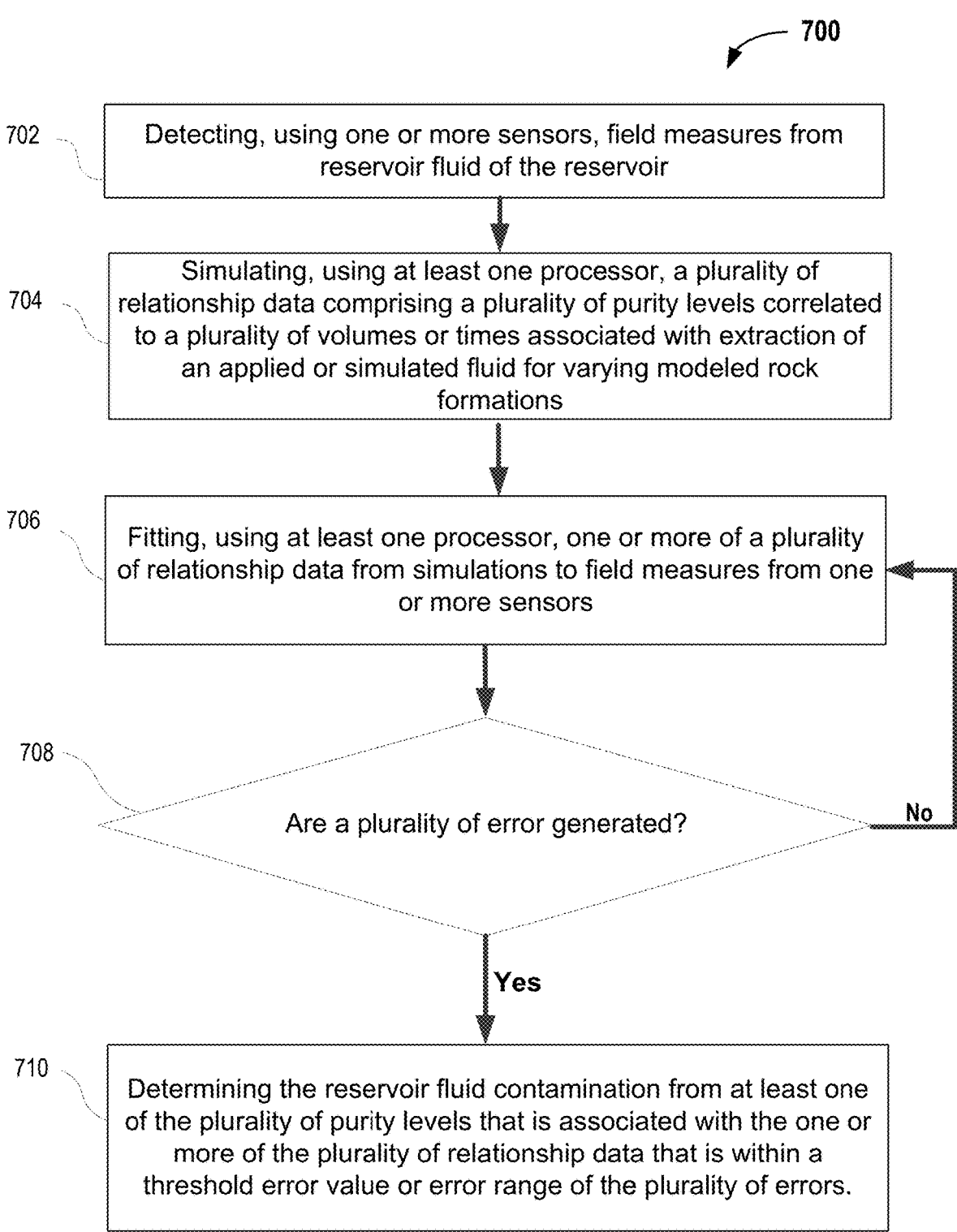
FIG. 7 illustrates a method for determining reservoir fluid contamination for a reservoir, according to at least one embodiment.

FIG. 7 illustrates a method 700 for determining reservoir fluid contamination for a reservoir, according to at least one embodiment. The method 700 includes detecting (702), using one or more sensors, field measures from reservoir fluid of the reservoir. A further step in the method is simulating (704), using at least one processor, relationship data that includes purity levels correlated to volumes of simulated or applied fluid for varying modeled rock formations. Further, the method 700 includes fitting (706), using the at least one processor, one or more of the relationship data to the field measures.

In at least one embodiment, a determination (708) is performed to check that errors associated with a fit between such data are generated. A fitting (706) operation may be repeated for the errors. Otherwise, a determining (710) step is performed for the reservoir fluid contamination from at least one of the purity levels that is associated with the one or more of the relationship data that is within a threshold error value or error range of the errors associated with the fit between such data in step 708.

Figure 8:
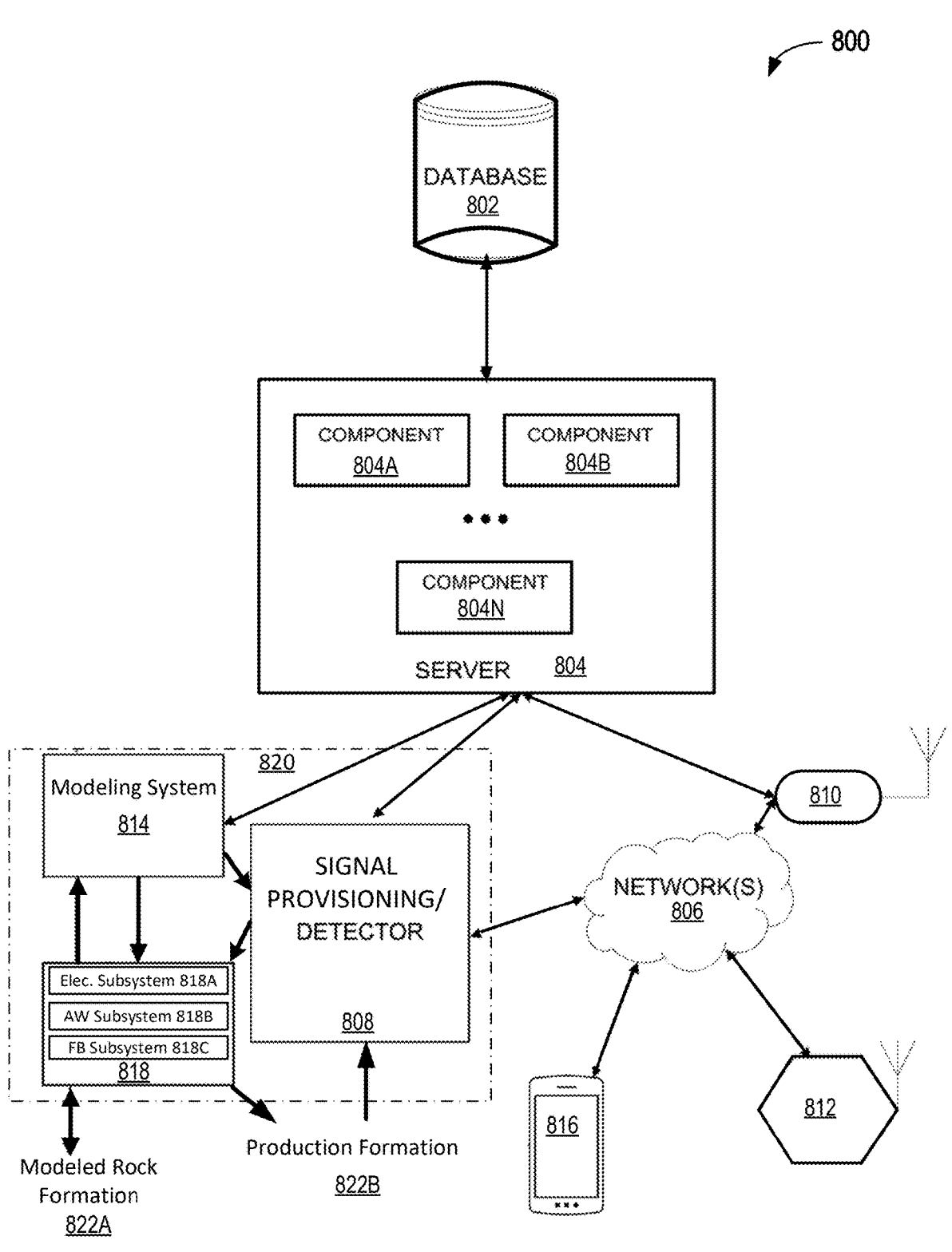
FIG. 8 illustrates computer and network aspects for a system for determining reservoir fluid contamination for a reservoir, according to at least one embodiment.

FIG. 8 illustrates computer and network aspects 800 for a system for determining reservoir fluid contamination for a reservoir, according to at least one embodiment. In at least one embodiment, these computer and network aspects 800 may include a distributed system. In at least one embodiment, a distributed system 800 may include one or more computing devices 812, 816. In at least one embodiment, one or more computing devices 812, 816 may be adapted to execute and function with a client application, such as with browsers or a stand-alone application, and are adapted to execute and function over one or more network(s) 806.

In at least one embodiment, a server 804, having components 804A-N may be communicatively coupled with computing devices 812, 816 via network 806 and via a receiver device, such as the signal provisioning or detector 808, if provided. In at least one embodiment, components 812, 816 include processors, memory and random-access memory (RAM). In at least one embodiment, server 804 may be adapted to operate services or applications to manage functions and sessions associated with database access 802 and associated with computing devices 812, 816. In at least one embodiment, server 804 may be associated with a signal provisioning or detector device 808 of a downhole tool 820.

In at least one embodiment, server 804 may be at a wellsite location, but may also be at a distinct location from a wellsite location. In at least one embodiment, such a server 804 may support a downhole tool or wireline system 820 for analysis of a production formation 822B within a downhole tool. Such a tool or wireline system 820 may be partly downhole and partly at a surface level. Such a tool or wireline system 820 may include subsystems 818A, B, C, to perform functions described throughout herein.

The subsystems may be modules that may be able to test or train a system on a surface level using modeled rock formation 822A that is a model or a simulation (or other representations, including images) thereof. The subsystem may be encased in one or more computing devices having at least one processor and memory so that the at least one processor can perform functions based in part on instructions from the memory executing in the at least one processor. In at least one embodiment, even though illustrated together, the system boundary 818 may be around a distributed system having subsystems 818A-C in different geographic locations, including downhole and surface areas.

A signal provisioning or detector device 808 of a downhole tool 820 is provided to test downhole production formations 822B using a reservoir fluid contamination determined using the system and method herein or using a liner function transformation that correlates at least one purity level and at least one field measure. In at least one embodiment, a system for determining reservoir fluid contamination for a reservoir includes a wireline system for the analysis, where such a system may be adapted to transmit, either through wires or wireless, information received therein, from a signal provisioning or detector device back to the surface.

In at least one embodiment, modeling performed using modeled rock formations 822A (and representations thereof) may be recorded within a modeling system 814. Required signals for a modeled rock formation 822A may be determined by a modeling system 814 and provided by one of subsystems 818A-C. The modeling system 814 can communicate to a signal provisioning or detector 808 and to subsystems 818A-C to enable testing of production formations 822B using the models stored in the modeling system 814. For example, each model may require specific signals to gather specific input to be used as testing data against trained ML/A algorithms.

Such signals may include electrical signals to be applied from an electrical subsystem 818A, air wave-based signals provided from an air wave-based subsystem 818B, and at least physical fluid-based testing for a production formation 822B provided from a fluid-based physical and simulation subsystem 818C. Detected results from the electrical signals may be used to determine field measures and to verify its fit within the modeled rock formation 822A.

In at least one embodiment, such information may be received in a receiver device and transmitted from there. In at least one embodiment, a server 804 may function as a signal provisioning or detector device (with a transmitter providing the actual signal and receiving a return signal) but may also perform other functions. In at least one embodiment, one or more component 804A-N may be adapted to function as a signal provisioning or detector device within a server 804. In at least one embodiment, one or more components 804A-N may include one or more processors and one or more memory devices adapted to function as a detector or receiver device, while other processors and memory devices in server 804 may perform other functions.

In at least one embodiment, a server 804 may also provide services or applications that are software-based in a virtual or a physical environment (such as to support the simulations referenced herein). In at least one embodiment, when server 804 is a virtual environment, then components 804A-N are software components that may be implemented on a cloud. In at least one embodiment, this feature allows remote operation of a system for analysis of a reservoir using a wireline system that is a tool, as discussed at least in reference to FIGS. 1-7. In at least one embodiment, this feature also allows for remote access to information received and communicated between any of aforementioned devices. In at least one embodiment, one or more components 804A-N of a server 804 may be implemented in hardware or firmware, other than a software implementation described throughout herein. In at least one embodiment, combinations thereof may also be used.

In at least one embodiment, one computing device 810-816 may be a smart monitor or a display having at least a microcontroller and memory having instructions to enable display of information monitored by a signal provisioning or detector device. In at least one embodiment, one computing device 810-812 may be a transmitter device to transmit directly to a receiver device or to transmit via a network 806 to a receiver device, such as the signal provisioning or detector 808, and to a server 804, as well as to other computing devices 812, 816.

In at least one embodiment, other computing devices 812, 816 may include portable handheld devices that are not limited to smartphones, cellular telephones, tablet computers, personal digital assistants (PDAs), and wearable devices (head mounted displays, watches, etc.). In at least one embodiment; other computing devices 812, 816 may operate one or more operating systems including Microsoft Windows Mobile®, Windows® (of any generation), and/or a variety of mobile operating systems such as iOS®, Windows Phone®, Android®, BlackBerry®, Palm OS®, and/or variations thereof.

In at least one embodiment, other computing devices 812, 816 may support applications designed as internet-related applications, electronic mail (email), short or multimedia message service (SMS or MMS) applications and may use other communication protocols. In at least one embodiment, other computing devices 812, 816 may also include general purpose personal computers and/or laptop computers running such operating systems as Microsoft Windows®, Apple Macintosh®, and/or Linux®. In at least one embodiment, other computing devices 812, 816 may be workstations running UNIX® or UNIX-like operating systems or other GNU/Linux operating systems, such as Google Chrome OS®. In at least one embodiment, thin-client devices, including gaming systems (Microsoft Xbox®) may be used as other computing device 812, 816.

In at least one embodiment, network(s) 806 may be any type of network that can support data communications using various protocols, including TCP/IP (transmission control protocol/Internet protocol), SNA (systems network architecture), IPX (Internet packet exchange), AppleTalk®, and/or variations thereof. In at least one embodiment, network(s) 806 may be a networks that is based on Ethernet, Token-Ring, a wide-area network, Internet, a virtual network, a virtual private network (VPN), a local area network (LAN), an intranet, an extranet, a public switched telephone network (PSTN), an infra-red network, a wireless network (such as that operating with guidelines from an institution like the Institute of Electrical and Electronics (IEEE) 802.11 suite of protocols, Bluetooth®, and/or any other wireless protocol), and/or any combination of these and/or other networks.

In at least one embodiment, a server 804 runs a suitable operating system, including any of operating systems described throughout herein. In at least one embodiment, server 804 may also run some server applications, including HTTP (hypertext transport protocol) servers, FTP (file transfer protocol) servers, CGI (common gateway interface) servers, JAVA® servers, database servers, and/or variations thereof. In at least one embodiment, a database 802 is supported by database server feature of a server 804 provided with front-end capabilities. In at least one embodiment, such database server features include those available from Oracle®, Microsoft®, Sybase®, IBM® (International Business Machines), and/or variations thereof.

In at least one embodiment, a server 804 can provide feeds and/or real-time updates for media feeds. In at least one embodiment, a server 804 is part of multiple server boxes spread over an area but functioning for a presently described process for analysis of a porous formation. In at least one embodiment, server 804 includes applications to measure network performance by network monitoring and traffic management. In at least one embodiment, a provided database 802 enables information storage from a wellsite, including user interactions, usage patterns information, adaptation rules information, and other information.

While techniques herein may be subject to modifications and alternative constructions, these variations are within spirit of present disclosure. As such, certain illustrated embodiments are shown in drawings and have been described above in detail, but these are not limiting disclosure to specific form or forms disclosed; and instead, cover all modifications, alternative constructions, and equivalents falling within spirit and scope of disclosure, as defined in appended claims.

Terms such as a, an, the, and similar referents, in context of describing disclosed embodiments (especially in context of following claims), are understood to cover both singular and plural, unless otherwise indicated herein or clearly contradicted by context, and not as a definition of a term. Including, having, and containing are understood to be open-ended terms (meaning a phrase such as, including, but not limited to) unless otherwise noted. Connected, when unmodified and referring to physical connections, may be understood as partly or wholly contained within, attached to, or joined, even if there is something intervening.

Recitation of ranges of values herein are merely intended to serve as a shorthand method of referring individually to each separate value falling within range, unless otherwise indicated herein and each separate value is incorporated into specification as if it were individually recited herein. In at least one embodiment, use of a term, such as a set (for a set of items) or subset unless otherwise noted or contradicted by context, is understood to be nonempty collection including one or more members. Further, unless otherwise noted or contradicted by context, term subset of a corresponding set does not necessarily denote a proper subset of corresponding set, but subset and corresponding set may be equal.

Conjunctive language, such as phrases of form, at least one of A, B, and C, or at least one of A, B and C, unless specifically stated otherwise or otherwise clearly contradicted by context, is otherwise understood with context as used in general to present that an item, term, etc., may be either A or B or C, or any nonempty subset of set of A and B and C. In at least one embodiment of a set having three members, conjunctive phrases, such as at least one of A, B, and C and at least one of A, B and C refer to any of following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present. In addition, unless otherwise noted or contradicted by context, terms such as plurality, indicates a state of being plural (such as, a plurality of items indicates multiple items). In at least one embodiment, a number of items in a plurality is at least two but can be more when so indicated either explicitly or by context. Further, unless stated otherwise or otherwise clear from context, phrases such as based on means based at least in part on and not based solely on.

Operations of methods in the Figures described herein can be performed in any suitable order unless otherwise indicated herein or otherwise clearly contradicted by context. In at least one embodiment, a method includes processes such as those processes described herein (or variations and/or combinations thereof) that may be performed under control of one or more computer systems configured with executable instructions and that may be implemented as code (e.g., executable instructions, one or more computer programs or one or more applications) executing collectively or exclusively on one or more processors, by hardware or combinations thereof.

In at least one embodiment, such code may be stored on a computer-readable storage medium. In at least one embodiment, such code may be a computer program having instructions executable by one or more processors. In at least one embodiment, a computer-readable storage medium is a non-transitory computer-readable storage medium that excludes transitory signals (such as a propagating transient electric or electromagnetic transmission) but includes non-transitory data storage circuitry (such as buffers, cache, and queues) within transceivers of transitory signals. In at least one embodiment, code (such as executable code or source code) is stored on a set of one or more non-transitory computer-readable storage media having stored thereon executable instructions (or other memory to store executable instructions) that, when executed (such as a result of being executed) by one or more processors of a computer system, cause computer system to perform operations described herein.

In at least one embodiment, a set of non-transitory computer-readable storage media includes multiple non-transitory computer-readable storage media and one or more of individual non-transitory storage media of multiple non-transitory computer-readable storage media lack all of code while multiple non-transitory computer-readable storage media collectively store all of code. In at least one embodiment, executable instructions are executed such that different instructions are executed by different processors in at least one embodiment, a non-transitory computer-readable storage medium store instructions and a main central processing unit (CPU) executes some of instructions while other processing units execute other instructions. In at least one embodiment, different components of a computer system have separate processors and different processors execute different subsets of instructions.

In at least one embodiment, computer systems are configured to implement one or more services that singly or collectively perform operations of processes described herein and such computer systems are configured with applicable hardware and/or software that enable performance of operations. In at least one embodiment, a computer system that implements at least one embodiment of present disclosure is a single device or is a distributed computer system having multiple devices that operate differently such that distributed computer system performs operations described herein and such that a single device does not perform all operations.

In at least one embodiment, even though the above discussion provides at least one embodiment having implementations of described techniques, other architectures may be used to implement described functionality, and are intended to be within scope of this disclosure. In addition, although specific responsibilities may be distributed to components and processes, they are defined above for purposes of discussion, and various functions and responsibilities might be distributed and divided in different ways, depending on circumstances.

In at least one embodiment, although subject matter has been described in language specific to structures and/or methods or processes, it is to be understood that subject matter claimed in appended claims is not limited to specific structures or methods described. Instead, specific structures or methods are disclosed as example forms of how a claim may be implemented.

From all the above, a person of ordinary skill would readily understand that the tool of the present disclosure provides numerous technical and commercial advantages and can be used in a variety of applications. Various embodiments may be combined or modified based in part on the present disclosure, which is readily understood to support such combination and modifications to achieve the benefits described above.

What is claimed is:

1. A system for determining reservoir fluid contamination for a reservoir, the system comprising:
  one or more sensors to detect field measures from reservoir fluid of the reservoir; and
  memory and at least one processor to execute instructions from the memory to cause the system to:
  simulate a plurality of relationship data comprising a plurality of purity levels correlated to a plurality of volumes or times associated with extraction of an applied or simulated fluid for varying modeled rock formations;
  fit one or more of the plurality of relationship data to the field measures to generate a plurality of errors; and
  determine the reservoir fluid contamination from at least one of the plurality of purity levels that is associated with the one or more of the plurality of relationship data that is within a threshold error value or an error range of the plurality of errors.

2. The system of claim 1, wherein the at least one processor executes the instructions from the memory to further cause the system to:
  project the plurality of errors to a distribution; and
  determine the threshold error value or the error range from a mean of the distribution.

3. The system of claim 1, wherein the at least one processor executes the instructions from the memory to further cause the system to:
  train one or more neural networks using at least the plurality of relationship data and the plurality of errors; and
  infer the reservoir fluid contamination for a new reservoir based in part on new field measures used with the one or more neural networks.

4. The system of claim 1, wherein the one or more sensors are adapted for sensing one or more of optical measures, sound speed measures, refractive index measures, density measures, and viscosity measures as part of the field measures from the reservoir fluid of the reservoir.

5. The system of claim 1, wherein the at least one processor executes the instructions from the memory to further cause the system to:
  generate a modeled rock formation to comprise pore structure using one or more images of a physical rock formation and using a plurality of physical variables; and
  simulate purity measures and volume or time measures for the modeled rock formation, the purity measures and the volume or time measures to be comprised in the plurality of relationship data.

6. The system of claim 1, wherein the varying modeled rock formations are generated from input data comprising one or more of a simulated formation pressure, a simulated formation porosity, a simulated formation permeability, a simulated formation flow rate, a simulated invasion parameter, a simulated anisotropy ratio, and simulated packers.

7. The system of claim 1, wherein the at least one processor executes the instructions from the memory to further cause the system to:
  apply a smoothening algorithm to the field measures to generate a smoothened version of the field measures; and
  fit an individual set of the smoothened version of the field measures to an individual set of the plurality of relationship data to identify a linear match, wherein the linear match is used in part to generate the plurality of errors.

8. The system of claim 1, wherein the at least one processor executes the instructions from the memory to further cause the system to:
  determine a purity level based in part on an extracted applied fluid through an individual physical rock formation having an injected contaminant and created as part of one or more physical rock formations from the varying modeled rock formations, the purity level contributing to the plurality of purity levels and a volume or a time of the extracted applied fluid contributing to the plurality of volumes or times.

9. The system of claim 1, wherein the at least one processor executes the instructions from the memory to further cause the system to:
  determine a volume or a time associated with the reservoir fluid from a sample taken from the reservoir; and
  determining the reservoir fluid contamination for the sample based in part on an extrapolation of the volume or the time to at least one of the plurality of relationship data after applying one of the plurality of errors.

10. The system of claim 1, wherein the at least one processor executes the instructions from the memory to further cause the system to:

extrapolate, using the reservoir fluid contamination, a further reservoir fluid contamination for future volumes or times of the reservoir fluid extracted from the reservoir.

11. A method for determining reservoir fluid contamination for a reservoir, the method comprising:

detecting, using one or more sensors, field measures from reservoir fluid of the reservoir;

simulating, using at least one processor, a plurality of relationship data comprising a plurality of purity levels correlated to a plurality of volumes or times associated with extraction of an applied or simulated fluid for varying modeled rock formations;

fitting, using the at least one processor, one or more of the plurality of relationship data to the field measures to generate a plurality of errors; and determining the reservoir fluid contamination from at least one of the plurality of purity levels that is associated with the one or more of the plurality of relationship data that is within a threshold error value or an error range of the plurality of errors.

12. The method of claim 11, further comprising:

projecting the plurality of errors to a distribution; and determining the threshold error value or the error range from a mean of the distribution.

13. The method of claim 11, further comprising:

training one or more neural networks using at least the plurality of relationship data and the plurality of errors; and inferring the reservoir fluid contamination for a new reservoir based in part on new field measures used with the one or more neural networks.

14. The method of claim 11, further comprising:

sensing, using the one or more sensors, one or more of optical measures, sound speed measures, refractive index measures, density measures, and viscosity measures as part of the field measures from the reservoir fluid of the reservoir.

15. The method of claim 11, further comprising:

generating a modeled rock formation to comprise pore structure using one or more images of a physical rock formation and using a plurality of physical variables; and simulating purity measures and volume or time measures for the modeled rock formation, the purity measures and the volume or time measures to be comprised in the plurality of relationship data.

16. The method of claim 11, wherein the varying modeled rock formations are generated from input data comprising one or more of a simulated formation pressure, a simulated formation porosity, a simulated formation permeability, a simulated formation flow rate, a simulated invasion parameter, a simulated anisotropy ratio, and simulated packers.

17. The method of claim 11, further comprising:

applying a smoothening algorithm to the field measures to generate a smoothened version of the field measures; and fitting an individual set of the smoothened version of the field measures to an individual set of the plurality of relationship data to identify a linear match, wherein the linear match is used in part to generate the plurality of errors.

18. The method of claim 11, further comprising:

providing one or more physical rock formations from the varying modeled rock formations;

injecting a contaminant into an individual physical rock formation;

extracting an applied fluid through the individual physical rock formation; and determining a purity level based in part on the extracted applied fluid, the purity level contributing to the plurality of purity levels and a volume of the extracted applied fluid contributing to the plurality of volumes.

19. The method of claim 11, further comprising:

obtaining a volume or a time of the reservoir fluid from a sample taken from the reservoir; and determining the reservoir fluid contamination for the sample based in part on an extrapolation of the volume or the time to at least one of the plurality of relationship data after applying one of the plurality of errors.

20. The method of claim 11, further comprising:

extrapolating, using the reservoir fluid contamination, a further reservoir fluid contamination for future volumes or times of the reservoir fluid extracted from the reservoir.

* * * * *